United States Patent [19]

Lundquist

[11] Patent Number: 5,660,837

[45] Date of Patent: Aug. 26, 1997

[54] PREPARING PHARMACEUTICAL FORMULATION IN FORM OF OIL-IN-WATER EMULSION

[75] Inventor: Stefan Lundquist, Stockholm, Sweden

[73] Assignee: Astra Aktiebolag, Sodertalje, Sweden

[21] Appl. No.: 460,046

[22] Filed: Jun. 2, 1995

Related U.S. Application Data

[62] Division of Ser. No. 379,486, filed as PCT/SE94/00926, Oct. 5, 1994.

[30] Foreign Application Priority Data

Oct. 7, 1993 [SE] Sweden ................................. 9303281

[51] Int. Cl.$^6$ ...................... A61K 9/107; A61K 31/425; B01J 13/00
[52] U.S. Cl. ...................... 424/400; 252/312; 252/314; 514/340; 514/365; 514/372; 514/938; 514/974
[58] Field of Search ................................. 252/312, 314; 424/400; 514/365, 372, 938, 974

[56] References Cited

U.S. PATENT DOCUMENTS

| | | | |
|---|---|---|---|
| 4,073,943 | 2/1978 | Wretlind et al. | 514/938 X |
| 4,493,847 | 1/1985 | Mizushima et al. | 514/938 X |
| 4,622,219 | 11/1986 | Haynes | 514/938 X |
| 4,647,586 | 3/1987 | Mizushima et al. | 514/938 X |
| 4,684,633 | 8/1987 | Imagawa et al. | 514/938 X |
| 4,760,096 | 7/1988 | Sakai et al. | 514/938 X |
| 4,801,455 | 1/1989 | List et al. | 424/400 |
| 5,089,268 | 2/1992 | Katz | 424/450 |
| 5,098,606 | 3/1992 | Nakajima et al. | 514/938 X |

FOREIGN PATENT DOCUMENTS

| | | |
|---|---|---|
| 0005121 | 10/1979 | European Pat. Off. . |
| 9102517 | 3/1991 | WIPO . |

*Primary Examiner*—Richard D. Lovering
*Attorney, Agent, or Firm*—White & Case

[57] ABSTRACT

The present invention is related to a pharmaceutical formulation which is an oil-in-water emulsion for parenteral and oral use which comprises (i) an emulsion-stabilizing surface active drug in high concentration;
(ii) optionally a pharmacologically inert oil;
(iii) optionally a surfactant;
(iv) water or a buffer; and
(v) an agent giving isotonicity to the final formulation;

the use of and a process for preparation of the formulation.

2 Claims, 2 Drawing Sheets

PREPARING PHARMACEUTICAL FORMULATION IN FORM OF OIL-IN-WATER EMULSION

This application is a divisional of application Ser. No. 08/379,486, filed on Jan. 30, 1995, under 37 U.S.C. 371 of PCT/SE94/00926 filed Oct. 5, 1994.

FIELD OF INVENTION

This invention relates to a novel pharmaceutical formulation comprising an emulsion-stabilizing surface active drug which may be administered parenterally or orally; and to the use of and a process for preparing said formulation.

BACKGROUND OF THE INVENTION

The present commercially available parenterally administered formulation of 5-(2-chloroethyl)-4-methylthiazole, hereafter abbreviated as CMZ, is a 0.8 w/v % solution of the edisilate salt of CMZ in 4 w/v % aqueous glucose. The product is not available in a more concentrated form because the incidence of hemolysis and venous thrombophlebitis is then unacceptably high. The solubility of the active ingredient is also too low at physiological pH. The low concentration of CMZ may require a large fluid load if the product is used for a prolonged period of time. This is a problem especially in patients with renal failure and those with fluid and electrolyte problems. Hence, the above mentioned problems have limited the product's usefulness in the clinic. Moreover, the presence of glucose is contraindicated in the treatment and/or prevention of neurodegeneration. Other undesirable properties of the commercially available product are the poor stability of the CMZ-edisilate at room temperature (the product must be stored at +4°–8° C.) and the substantial sorption of CMZ by intravenous infusion giving sets. This sorption to plastics results in a safety problem in the clinic, especially when treating disorders requiring very accurate dosing. Finally, the oral liquid dosage form, a 5 w/v % syrup of CMZ-edisilate, also has a number of disadvantages such as poor stability at room temperature and a low level of patient acceptance due to the acidity and bitter taste of the product. There is accordingly a great need for an improved product both from a pharmaceutical and clinical point of view.

DESCRIPTION OF THE INVENTION

The problems mentioned above have surprisingly been solved by a novel formulation. Thus, the object of the invention is to provide a novel, clinically and pharmaceutically acceptable and useful formulation which is an oil-in-water emulsion for parenteral and oral use which comprises (i) an emulsion-stabilizing surface active drug in high concentration;

(ii) optionally a pharmacologically inert oil;

(iii) optionally a surfactant;

(iv) water or a buffer; and (v) an agent giving isotonicity to the final formulation.

The present invention is preferably related to emulsion-stabilizing surface active drugs having an anti-convulsant or sedative-hypnotic effect or drugs for preventing and/or treating neurodegeneration caused by acute and chronic neuropsychiatric disorders characterised by progressive processes that sooner or later lead to neuronal cell death and dysfunction. Such disorders include stroke; cerebral ischaemia; dysfunctions resulting from brain and/or spinal trauma; hypoxia and anoxia, such as from drowning, and including perinatal and neonatal hypoxic asphyxial brain damage; multi-infarct dementia; AIDS dementia; neurodegenerative diseases such as Alzheimer's disease, Parkinson's disease, Huntington's chorea, epilepsy, multiple sclerosis and amytrophic lateral sclerosis; brain dysfunction in connection with surgery involving extracorporeal circulation or in connection with brain surgery, including endarterectomy of the carotid arteries; and CNS dysfunctions as a result of exposure to neurotoxins or radiation. This utility is manifested, for example, by the ability of the claimed formulation to inhibit delayed neuronal death in the gerbil bilateral occlusion model of ischaemia.

Preferred emulsion-stabilizing surface active drugs are the CMZ-base which is an oil at room temperature, and/or some analogues thereof which are oils at room temperature, namely 5-(2-chloroethyl)-4-methyloxazole, 5-(2-chloroethyl)-2,4-dimethyloxazole, 5-(2-chloroethyl)-2,4-dimethylthiazole or 5-(2-chloro-1-hydroxyethyl)-4-methylthiazole or its optical isomers, the surface active drug functioning, besides having a pharmacological effect, as a stabilizing surfactant or co-surfactant at the large interface in an oil in water emulsion system or in another aspect of the invention, functioning as the actual oil phase in an emulsion system.

The use of this invention is, however, by no means limited to the above mentioned drugs but could also be used to include any other drug which displays suitable amphiphilic and emulsion-stabilizing properties.

A conventional pharmacologically inert oil is included as a component in the formulation when the emulsion-stabilizing drug is not itself used as the internal oil phase.

A conventional surfactant is included as a component in the formulation when the drug functions as the internal oil phase of the emulsion.

The agent giving isotonicity to the final formulation is preferably glycerol and/or sorbitol.

By means of the present invention the undesirable properties of both the parenteral and the oral dosage form, mentioned in the background of the invention, can be avoided. Certain compounds, because of their chemical stucture, have a tendency to accumulate at the boundary between two phases. Such compounds are termed amphiphiles, surface-active agents or surfactants. The adsorption at various interfaces results in fundamental changes in the nature of the interface which are of considerable importance in different contexts. For example, in an emulsion the adsorption of a surfactant at the oil-water interface lowers the interfacial tension thereby aiding in the dispersal of the oil into droplets of a small size and helping to maintain the droplets in a dispersed state. Unless the interfacial tension is zero, there is a tendency for the oil droplets to coalesce to reduce the area of oil-water contact, but the presence of the surfactant monolayer at the surface of the droplets reduces the possibility of collisions leading to droplet coalescence and consequently impaired stability of the system. However, not all conventional surfactants display a stabilizing effect sufficient to allow storage for a long period of time (typically two years) of pharmaceutically interesting two-phase systems such as for example emulsions. The geometrical shape of the amphiphilic molecule and the presence of any substituents in said molecule can have an appreciable effect on its stabilizing properties. Surprisingly, it has been found that e.g. CMZ and said analogues display excellent emulsion-stabilizing properties which allow emulsions of these compounds to be stored for a long period of time. Due to the geometrical shape and the amphiphilic properties of the drug molecule it is adsorbed at the surface of the droplets in the emulsion, forming a rigid and tightly packed interfacial film thereby reducing the possibility of collisions leading to droplet coalescence and consequently impaired stability of the system.

It has also surprisingly been found that a number of other drugs with hydrophobic portions comprising aromatic and/or heterocyclic ring systems or a steroid skeleton also display good emulsion-stabilizing properties.

Examples of the types of drugs, besides CMZ and its analogues, which have been found beneficial to use as emulsion-stabilizing agents include: antidepressants, neuroleptics, immunosuppressants, immunomodulators, antibiotics, antiinflammatory agents, proton pump inhibitors, calcium channel blockers, such as felodipine, and beta blockers.

Since it is usually observed that mixtures of conventional surfactants form even more stable systems than do single surfactants, even with very dilute emulsions, it has in some cases been found beneficial to use emulsion-stabilizing surface active drugs as co-surfactants together with any conventional pharmaceutically acceptable non-ionic surfactants, such as the poloxamers F68, F127 or L92 or polyoxyethylene sorbitan fatty acid esters, polyoxyethylene stearates or sorbitan fatty acid esters; but preferably together with phospholipids, such as egg yolk phospholipids, soya phospholipids, synthetic phosphatidylcholines (e.g. dimyristoyl-phosphatidylcholine (DMPC) and/or dipalmitoyl-phosphatidylcholine (DPPC)) or purified phosphatidyl-cholines of vegetable origin.

If this principle is fully used by a person skilled in the art it is possible to manufacture a stable two-phase system like e.g. an emulsion of any appropriate drug mentioned above, where the stabilizing effect is due to the surface active drug alone or the surface active drug together with an optional surfactant mentioned above, and at the same time making use of the large interface in this kind of system to incorporate a high concentration of said surface active drug. In another aspect of the invention, CMZ and the above mentioned analogues or any other appropriate drug which is in the liquid state, could also function as the actual oil phase in an emulsion system in that way making it possible to incorporate a high concentration of the drug. In the latter case said formulation is stabilized by any of the above mentioned conventional surfactants.

Figure 1A:
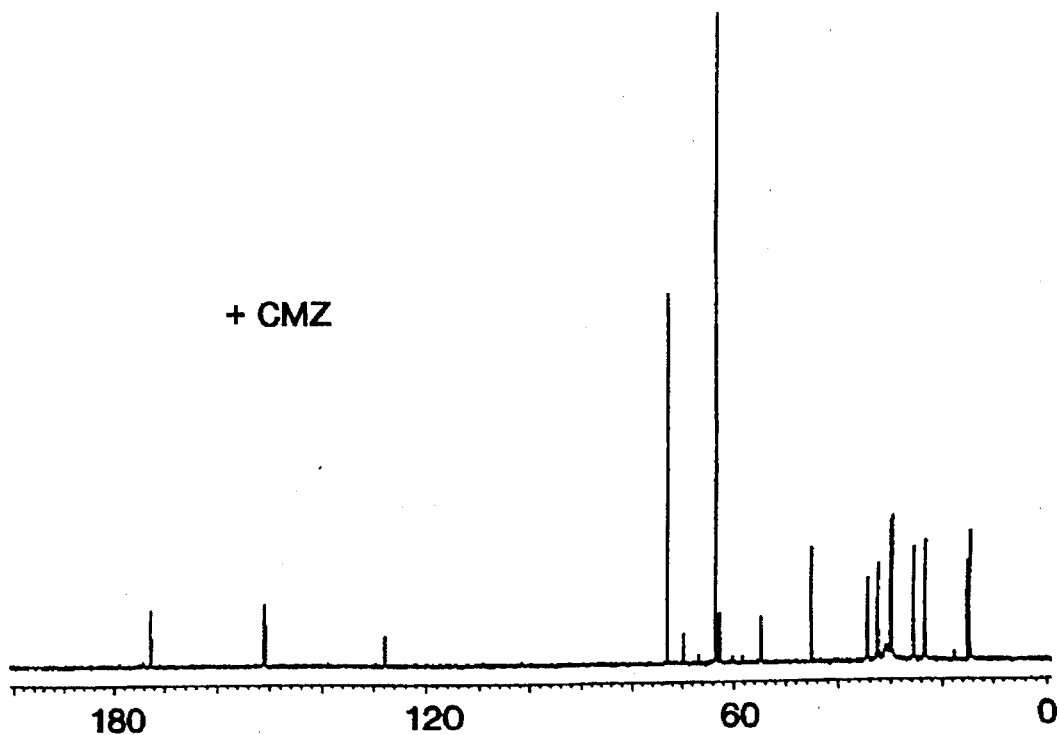
FIG. 1A shows the $^{13}$C-NMR spectra of an emulsion with CMZ.
Figure 1B:
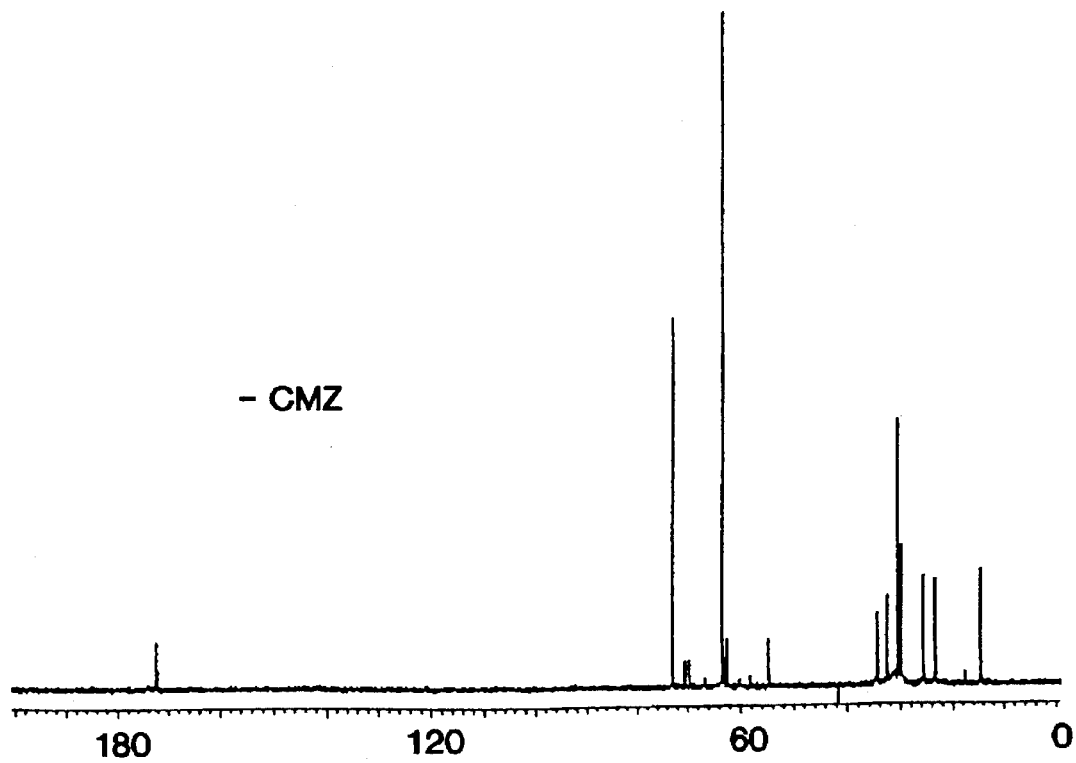
FIG. 1B shows the $^{13}$C-NMR spectra of an emulsion without CMZ.
Figure 2:
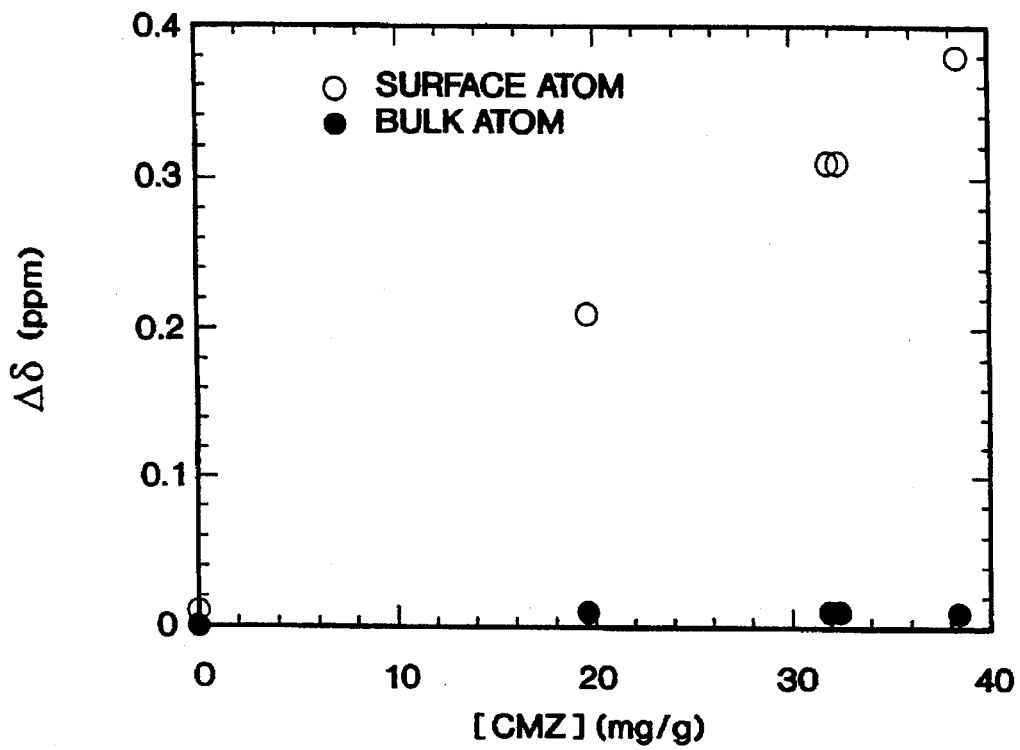
FIG. 2 shows changes in the chemical shifts of the carbonyl carbons of a phospholipid, located at the interface in the emulsion system, in the presence of CMZ.
Figure 3:
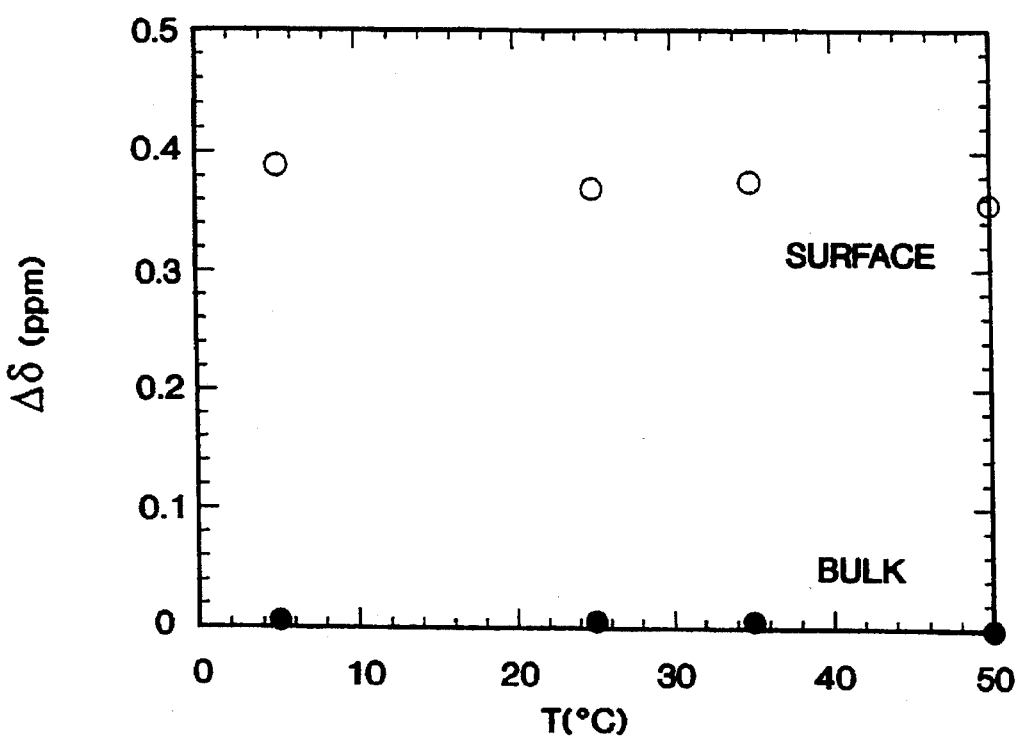
FIG. 3 shows the effects of shifter differences are essentially independent of temperature.

The location of the drug in the formulation in the former case can be established by known techniques such as $^{13}$C-NMR and a spectra of an emulsion with and without CMZ is shown in FIG. 1. Using $^{13}$C-NMR chemical shift determinations, it is possible to obtain information on the location of the CMZ-molecule in the emulsion system. For example, according to FIG. 2 the chemical shifts of the carbonyl carbons of a phospholipid, which are located at the interface in the emulsion system, is changed in the presence of CMZ. In fact, there is a linear relationship between the concentration of CMZ in the system and the change in the chemical shifts of the carbonyl carbons (FIG. 2). The chemical shifts of the methylene carbons, being located in the core of the emulsion droplets is essentially unaffected by the presence of CMZ which can also be seen in FIG. 2. Notably, the effects of CMZ on these shift differences are essentially independent of temperature, as shown in FIG. 3. Since the chemical shift of a nucleus depends on its immediate environment ($\leq 5$ Å), these findings clearly show that CMZ is primarily located in the surface region of the emulsion droplets.

Surprisingly, it has been found that the presence of emulsion-stabilizing surface active drugs at the interface of an emulsion not only produces emulsions with excellent physical stability but also makes it possible to improve poor chemical stability of the drug in some cases, rendering it possible to prolong storage of these novel formulations of e.g. CMZ and/or any of the analogues or any other appropriate drug at room temperature. Improved chemical stability of the drug as well as a good physical stability of the formulation have also been obtained when e.g. CMZ and/or any of the analogues or any other appropriate drug which is in the liquid state has been used as the actual oil phase of an emulsion, thus allowing for a prolonged storage at room temperature. It has also become possible to substantially increase the drug concentration in these systems compared to a water solution of the drug and at the same time maintaining a physiologically acceptable pH thereby rendering these novel formulations clinically more useful. It has furthermore become possible to replace glucose with glycerol, which is not contraindicated in the treatment and/or prevention of neurodegeneration. Many of the above mentioned surface active drugs are known to cause hemolysis as well as thrombophlebitis when administered parenterally as water solutions. Consequently, it was most surprising and clinically important when it was found that these novel formulations according to the present invention made it possible to greatly reduce the incidence of hemolysis and thrombophlebitis and even in some cases made the symptoms to completely disappear without reducing the pharmacological effect of the drug. In addition to this a number of other clinically and pharmaceutically undesirable properties were successfully dealt with by using the novel formulation according to the present invention. Hence, the safety of e.g. CMZ in the clinic was improved by a substantially reduced sorption of the drug by intravenous infusion giving sets and moreover by giving the emulsion orally it was found that this type of formulation was also capable of improving the conventional liquid oral dosage form by a considerably better masking of the bitter taste of CMZ and at the same time solving the problem of the acidity of the syrup.

Another object of the present invention is a process for the preparation of the novel formulation comprising the following steps;

in the case where the emulsion-stabilizing surface active drug is not itself used as the internal oil phase by adding the emulsion-stabilizing surface active drug and an optional conventional surfactant to a two-phase, oil-water-system at room temperature;

allowing the emulsion-stabilizing surface active drug or the emulsion-stabilizing surface active drug together with the conventional surfactant to equilibrate at the interface;

adding an agent giving isotonicity to the final formulation; and homogenizing by high pressure technique whereby a stable emulsion is obtained which has a droplet size distribution where the main fraction is below 200 nm;

or in the case where the drug functions as the internal oil phase of the system by dispersing the emulsion-stabilizing surface active drug together with a conventional surfactant in water at room temperature;

allowing said surfactant to equilibrate at the interface;

adding an agent giving isotonicity to the final formulation; and homogenizing by high pressure technique; whereby a stable emulsion is obtained which has a droplet size distribution where the main fraction is below 200 nm.

The resulting formulation is easily sterile filtered. Instead of water a sodium carbonate buffer may be used.

If the drugs are sensitive to heat, a prerequisite is that these systems can readily be: a) sterile filtered which means that the main fraction of the size distribution of the droplets must be below 200 nm, preferably below a 100 nm (determined by dynamic light scattering, b) prepared without the addition of heat, which is usually required in a process like this (typically 60°–70° C.). Hence, by the inherent characteristics of the novel formulation according to the present invention it is possible to prepare these systems at room temperature with a mean droplet size below 100 nm (allowing sterile filtration) without the additional help of solvents or co-solvents during the process of manufacturing.

This novel formulation comprises in general the emulsion-stabilizing surface active drug in a concentration from about 0.01 to 5% w/v.

More particularly, the novel formulation of the invention comprises: a) the emulsion-stabilizing surface active drug in an amount of from about 0.01 to 5.0 g per 100 ml of the final formulation; b) if the drug is not itself used as the internal oil phase a pharmacologically inert oil may be used in an amount of from about 0.5 to 40 g per 100 ml of the final formulation, said oil being selected from any pharmaceutically acceptable oils, such as soybean oil, safflower oil, sesame oil, peanut oil, cottonseed oil, borago oil, sunflower oil, corn oil, olive oil, medium chain triglycerides (such as Miglyol®), or acetylated monoglycerides; c) a surfactant in an amount of from about 0.1 to 20 g per 100 ml of the final formulation, said surfactant being selected from any pharmaceutically acceptable non-ionic surfactants, such as the poloxamers F68, F127 or L92 or polyoxyethylene sorbitan fatty acid esters, polyoxyethylene stearates or sorbitan fatty acid esters; but preferably together with phospholipids, such as egg yolk phospholipids, soya phospholipids, synthetic phosphatidylcholines (e.g. dimyristoyl-phosphatidylcholine (DMPC) and/or dipalmitoyl-phosphatidylcholine (DPPC)) or purified phosphatidyl-cholines of vegetable origin; or any other suitable surfactants acceptable to regulatory agencies (GRAS status); d) water for injection or suitable buffer; e) preferred agents to give isotonicity to the final formulation are glycerol and/or sorbitol.

The amount of CMZ-base and/or analogues is conveniently from about 0.5 to 3.0 g per 100 ml of the final formulation, preferably 0.5 to 2.0 g per 100 ml of the final formulation. The amount of a pharmacologically inert oil, if any, is conveniently from about 2.0 to 30 g per 100 ml of the final formulation, preferably 2.0 to 20 g per 100 ml of the final formulation. The amount of surfactant, if any, is conveniently from about 1.0 to 10 g per 100 ml of the final formulation, preferably 2.0 to 5.0 g per 100 ml of the final formulation. The amount of the isotonicity agent is from about 1.0 to 5.0 g per 100 ml of the final formulation.

The administration in the novel method of treatment of this invention may conveniently be oral or parenteral at a dosage level of, for example, about 1 to 3000 mg/kg, preferably about 10 to 1000 mg/kg and especially about 25 to 250 mg/kg and may be administered on a regimen of 1 to 4 doses or treatments per day. The dose will depend on the route of administration preferred routes being oral or intravenous administration. It will be appreciated that the severity of the disease, the age of the patient and other factors normally considered by the attending physician will influence the individual regimen and dosage most appropriate for a particular patient.

In an acute situation, this novel method of treatment may also involve parenteral administration of the drug in the form of prepacked unit doses.

Preferred embodiments of the invention will now be described by way of example, which however are not limitative:

EXAMPLES 1–2

Oil-in-water emulsions of CMZ for intravenous and oral use were prepared from the following components:

|  | Ex. 1 |
|---|---|
| CMZ | 0.5 g |
| DMPC | 2.0 g |
| DPPC | 0.5 g |
| Miglyol 812 | 2.5 g |
| Glycerol | 4.0 g |
| Water for injection to | 100 ml |

Adjustment to physiological pH with 1M sodium hydroxide.

|  | Ex. 2 |
|---|---|
| CMZ | 0.5 g |
| DMPC | 2.0 g |
| DPPC | 0.5 g |
| Miglyol 812 | 2.5 g |
| Glycerol | 2.0 g |
| Sodium carbonate buffer pH 7.0 to | 100 ml |

In a first step the emulsion-stabilizing drug and a surfactant were added to a two-phase system, oil-water, at room temperature and were subsequently allowed to equilibrate at the interface. This formulation, together with additional indicated components in the formula, was homogenized and the resulting emulsion was stable and had an average droplet size below 100 nm and could easily be sterile filtered (200 nm filter).

EXAMPLES 3–8

Oil-in-water emulsions were prepared as described in Examples 1–2 with the following components:

|  | Ex. 3 | Ex. 4 | Ex. 5 |
|---|---|---|---|
| 5-(2-chloroethyl)-4-methyloxazole | 0.05 g | 2.0 g | 4.0 g |
| DMPC | 0.4 g | 2.0 g | 4.0 g |
| DPPC | 0.1 g | 0.5 g | 1.0 g |
| Miglyol 812 | 1.0 g | 5.0 g | 10.0 g |
| Glycerol | 5.0 g | 3.0 g | 2.5 g |
| Water for injection to | 100 ml | 100 ml | 100 ml |
| Adjustment to physiological pH with 1M sodium hydroxide |  |  |  |

|  | Ex. 6 | Ex. 7 | Ex. 8 |
| --- | --- | --- | --- |
| CMZ | 0.05 g | 2.0 g | 4.0 g |
| DMPC | 0.4 g | 2.0 g | 4.0 g |
| DPPC | 0.1 g | 0.5 g | 1.0 g |
| Miglyol 812 | 1.0 g | 5.0 g | 10.0 g |
| Glycerol | 2.5 g | 1.5 g | 1.25 g |
| Sodium carbonate buffer pH 7.0 to | 100 ml | 100 ml | 100 ml |

EXAMPLES 9–12

Oil-in-water emulsions were prepared as described in Examples 1–2 with the following components:

|  | Ex. 9 |
| --- | --- |
| 5-(2-chloroethyl)-2,4-dimethyloxazole | 2.0 g |
| DMPC | 2.0 g |
| DPPC | 0.5 g |
| Soybean oil | 5.0 g |
| Glycerol | 3.0 g |
| Water for injection to | 100 ml |
| Adjustment to physiological pH with 1M sodium hydroxide | |

|  | Ex. 10 |
| --- | --- |
| CMZ | 2.0 g |
| DMPC | 2.0 g |
| DPPC | 0.5 g |
| Safflower oil | 5.0 g |
| Glycerol | 3.0 g |
| Water for injection to | 100 ml |
| Adjustment to physiological pH with 1M sodium hydroxide | |

|  | Ex. 11 |
| --- | --- |
| 5-(2-chloroethyl)-2,4-dimethylthiazole | 2.0 g |
| DMPC | 2.0 g |
| DPPC | 0.5 g |
| Cotton seed oil | 5.0 g |
| Glycerol | 3.0 g |
| Water for injection to | 100 ml |
| Adjustment to physiological pH with 1M sodium hydroxide | |

|  | Ex. 12 |
| --- | --- |
| CMZ | 2.0 g |
| DMPC | 2.0 g |
| DPPC | 0.5 g |
| Soy bean oil | 5.0 g |
| Acetylated monoglycerides | 2.5 g |
| Glycerol | 3.0 g |
| Water for injection to | 100 ml |
| Adjustment to physiological pH with 1M sodium hydroxide | |

EXAMPLES 13–16

Oil-in-water emulsions, according to Examples 9–12, were prepared with the only difference that a sodium carbonate buffer pH 7.0 was used to a final volume of 100 ml instead of water for injection and the amount of glycerol was reduced to 1.5 g per 100 ml of the final formulations.

EXAMPLES 17–20

Oil-in-water emulsions were prepared as described in Examples 1–2 with the following components:

|  | Ex. 17 |
| --- | --- |
| 5-(2-chloro-1-hydroxy-ethyl)-4-methylthiazole | 2.0 g |
| Egg yolk phospholipids | 2.5 g |
| Miglyol 812 | 5.0 g |
| Glycerol | 3.0 g |
| Water for injection to | 100 ml |
| Adjustment to physiological pH with 1M sodium hydroxide | |

|  | Ex. 18 |
| --- | --- |
| CMZ | 2.0 g |
| Soya phospholipids | 2.5 g |
| Miglyol 812 | 5.0 g |
| Glycerol | 3.0 g |
| Water for injection to | 100 ml |
| Adjustment to physiological pH with 1M sodium hydroxide | |

|  | Ex. 19 |
| --- | --- |
| Felodipine* | 0.1 g |
| Soy phosphatidylcholine | 2.5 g |
| Soy bean oil | 10.0 g |
| Glycerol | 2.5 g |
| Water for injection to | 100 ml |
| Adjustment to physiological pH with 1M sodium hydroxide | |

*Felodipine is 4-(2,3-Dichlorophenyl)-1,4-dihydro-2,6-dimethyl-3,5-pyridinedicarboxylic acid ethyl methyl ester.

|  | Ex. 20 |
| --- | --- |
| CMZ | 2.0 g |
| Poloxamer F68 | 2.5 g |
| Miglyol 812 | 5.0 g |
| Glycerol | 3.0 g |
| Water for injection to | 100 ml |
| Adjustment to physiological pH with 1M sodium hydroxide | |

EXAMPLES 21–24

Oil-in-water emulsions were prepared according to Examples 17–20 with the only difference that a sodium carbonate buffer pH 7.0 was used to a final volume of 100 ml instead of water for injection and the amount of glycerol was reduced to 1.5 g per 100 ml of the final formulations.

EXAMPLES 25–26

Oil in water emulsions, where the emulsion-stabilizing drug was used as the sole stabilizing agent in the system, were prepared from the following components:

|  | Ex. 25 |
| --- | --- |
| CMZ | 0.5 g |
| Miglyol 812 | 2.5 g |
| Glycerol | 4.0 g |
| Water for injection to | 100 ml |
| Adjustment to physiological pH with 1M sodium hydroxide. | |

|  | Ex. 26 |
| --- | --- |
| CMZ | 0.5 g |
| Miglyol 812 | 2.5 g |
| Glycerol | 2.0 g |
| Sodium carbonate buffer pH 7.0 to | 100 ml |

In a first step the emulsion-stabilizing drug was added to a two-phase system, oil-water, at room temperature and was subsequently allowed to equilibrate at the interface. This formulation, together with additional indicated components in the formula, was homogenized and the resulting emulsion was stable and had an average droplet size below 100 nm and could easily be sterile filtered (200 nm filter).

EXAMPLES 27–30

Oil in water emulsions were prepared as described in Examples 25–26 with the following components:

|  | Ex. 27 |
| --- | --- |
| 5-(2-chloro-1-hydroxy-ethyl)-4-methylthiazole | 2.0 g |
| Miglyol 812 | 5.0 g |
| Glycerol | 3.0 g |
| Water for injection to | 100 ml |
| Adjustment to physiological pH with 1M sodium hydroxide | |

|  | Ex. 28 |
| --- | --- |
| CMZ | 2.0 g |
| Miglyol 812 | 5.0 g |
| Glycerol | 3.0 g |
| Water for injection to | 100 ml |
| Adjustment to physiological pH with 1M sodium hydroxide | |

|  | Ex. 29 |
| --- | --- |
| 5-(2-chloroethyl)-4-methyloxazole | 2.0 g |
| Miglyol 812 | 5.0 g |
| Glycerol | 3.0 g |
| Water for injection to | 100 ml |
| Adjustment to physiological pH with 1M sodium hydroxide | |

|  | Ex. 30 |
| --- | --- |
| CMZ | 2.0 g |
| Miglyol 812 | 5.0 g |
| Glycerol | 3.0 g |
| Water for injection to | 100 ml |
| Adjustment to physiological pH with 1M sodium hydroxide | |

EXAMPLES 31–32

Emulsions where the drug functions as the internal oil-phase of the system were prepared from the following components:

|  | Ex. 31 |
| --- | --- |
| CMZ | 0.5 g |
| DMPC | 2.0 g |
| DPPC | 0.5 g |
| Glycerol | 4.0 g |
| Water for injection to | 100 ml |
| Adjustment to physiological pH with 1M sodium hydroxide | |

|  | Ex. 32 |
| --- | --- |
| 5-(2-chloroethyl)-2,4-dimethyloxazole | 0.5 g |
| DMPC | 2.0 g |
| DPPC | 0.5 g |
| Glycerol | 2.0 g |
| Sodium carbonate buffer pH 7.0 to | 100 ml |

In a first step the drug was dispersed in water at room temperature. An emulsion was then prepared from the resulting drug-water dispersion, together with additional indicated components in the formula. The resulting emulsion was stable and had an average droplet size below 100 nm and could easily be sterile filtered (200 nm filter).

EXAMPLES 33–38

Emulsions according to Examples 31–32 were prepared with the following components:

|  | Ex. 33 | Ex. 34 | Ex. 35 |
| --- | --- | --- | --- |
| CMZ | 0.05 g | 2.0 g | 4.0 g |
| DMPC | 0.4 g | 2.0 g | 4.0 g |
| DPPC | 0.1 g | 0.5 g | 1.0 g |
| Glycerol | 5.0 g | 3.0 g | 2.5 g |
| Water for injection to | 100 ml | 100 ml | 100 ml |
| Adjustment to physiological pH with 1M sodium hydroxide | | | |

|  | Ex. 36 | Ex. 37 | Ex. 38 |
| --- | --- | --- | --- |
| 5-(2-chloroethyl)-2,4-dimethylthiazole | 0.05 g | 2.0 g | 4.0 g |
| DMPC | 0.4 g | 2.0 g | 4.0 g |
| DPPC | 0.1 g | 0.5 g | 1.0 g |

-continued

|  | Ex. 36 | Ex. 37 | Ex. 38 |
|---|---|---|---|
| Glycerol | 2.5 g | 1.5 g | 1.25 g |
| Sodium carbonate buffer pH 7.0 to | 100 ml | 100 ml | 100 ml |

EXAMPLES 39–42

Emulsions according to Examples 31–32 were prepared with the following components:

|  | Ex. 39 |
|---|---|
| CMZ | 2.0 g |
| Egg yolk phospholipids | 2.5 g |
| Glycerol | 3.0 g |
| Water for injection to | 100 ml |
| Adjustment to physiological pH with 1M sodium hydroxide | |

|  | Ex. 40 |
|---|---|
| 5-(2-chloro-1-hydroxy-ethyl)-4-methylthiazole | 2.0 g |
| Soya phospholipids | 2.5 g |
| Glycerol | 3.0 g |
| Water for injection to | 100 ml |
| Adjustment to physiological pH with 1M sodium hydroxide | |

|  | Ex. 41 |
|---|---|
| CMZ | 2.0 g |
| Soy phosphatidylcholine | 2.5 g |
| Glycerol | 3.0 g |
| Water for injection to | 100 ml |
| Adjustment to physiological pH with 1M sodium hydroxide | |

|  | Ex. 42 |
|---|---|
| CMZ | 2.0 g |
| Pluronic F68 | 2.5 g |
| Glycerol | 3.0 g |
| Water for injection to | 100 ml |
| Adjustment to physiological pH with 1M sodium hydroxide | |

EXAMPLES 43–46

Emulsions according to Examples 39–42 were prepared with the only difference that a sodium carbonate buffer pH 7.0 was used to a final volume of 100 ml instead of water for injection and the amount of glycerol was reduced to 1.5 g per 100 ml of the final formulations.

I claim:

1. A process for the preparation of a pharmaceutical formulation in the form of an oil-in-water emulsion comprising the steps of:
   (a) in the case where an emulsion-stabilizing surface active drug is not itself used as the internal oil phase,
      (i) adding the emulsion-stabilizing surface active drug and an optimal conventional surfactant to a two-phase, oil-water system at room temperature;
      (ii) allowing the emulsion-stabilizing surface active drug or the emulsion-stabilizing surface active drug together with the conventional surfactant to equilibrate at an interface of oil and water;
      (iii) adding an agent giving isotonicity to the final formulation; and
      (iv) homogenizing by high pressure technique;
   whereby a stable emulsion is-obtained which has a droplet size distribution where the main fraction is below 200 nm; or
   (b) in the case where the drug functions as the internal oil phase of the system,
      (i) dispersing the emulsion-stabilizing surface active drug together with a conventional surfactant in water at room temperature;
      (ii) allowing the surfactant to equilibrate at the interface of oil and water;
      (iii) adding an agent giving isotonicity to the final formulation; and
      (iv) homogenizing by high pressure technique;
   whereby a stable emulsion is obtained which has a droplet size distribution where the main fraction is below 200 nm.

2. The process according to claim 1 further comprising an additional final sterile filtering step.

* * * * *

UNITED STATES PATENT AND TRADEMARK OFFICE
CERTIFICATE OF CORRECTION

PATENT NO.   : 5,660,837
DATED        : August 26, 1997
INVENTOR(S)  : Stefan Lundquist It is certified that error appears in the above-indentified patent and that said Letters Patent is hereby corrected as shown below:

Col. 12, line 23, change "optimal" to --optional--; and

Col. 12, line 32, delete "-" in "is-obtained."

Signed and Sealed this

Twelfth Day of May, 1998

Attest:

BRUCE LEHMAN

Attesting Officer

Commissioner of Patents and Trademarks